US011207031B2

(12) United States Patent
Mehta et al.

(10) Patent No.: US 11,207,031 B2
(45) Date of Patent: Dec. 28, 2021

(54) HEART SIGNAL WAVEFORM PROCESSING SYSTEM AND METHOD (71) Applicant: CARDIONOMOUS LLC, Miami, FL (US)

(72) Inventors: Sameer Mehta, Miami, FL (US); Francisco J. Fernandez, Santiago (CL)

(73) Assignee: CARDIONOMOUS LLC, Miami, FL (US)

( * ) Notice: Subject to any disclaimer, the term of this patent is extended or adjusted under 35 U.S.C. 154(b) by 0 days.

(21) Appl. No.: 16/654,948

(22) Filed: Oct. 16, 2019

(65) Prior Publication Data

US 2020/0113467 A1 Apr. 16, 2020

Related U.S. Application Data (60) Provisional application No. 62/746,282, filed on Oct. 16, 2018.

(51) Int. Cl.
| | |
|---|---|
| *A61B 5/28* | (2021.01) |
| *A61B 5/00* | (2006.01) |
| *G06N 20/00* | (2019.01) |
| *G16H 50/20* | (2018.01) |
| *G16H 50/30* | (2018.01) |
| *G16H 40/67* | (2018.01) |
| *A61B 5/35* | (2021.01) |
| *A61B 5/282* | (2021.01) |
| *A61B 5/316* | (2021.01) |
| *A61B 5/349* | (2021.01) |
| *A61B 5/364* | (2021.01) |

(52) U.S. Cl.
CPC ............ *A61B 5/7267* (2013.01); *A61B 5/282* (2021.01); *A61B 5/316* (2021.01); *A61B 5/349* (2021.01); *A61B 5/35* (2021.01); *A61B 5/364* (2021.01); *A61B 5/681* (2013.01); *A61B 5/6893* (2013.01); *A61B 5/6898* (2013.01); *A61B 5/7264* (2013.01); *G06N 20/00* (2019.01); *G16H 40/67* (2018.01); *G16H 50/20* (2018.01); *G16H 50/30* (2018.01); *A61B 5/0006* (2013.01)

(58) Field of Classification Search
CPC . A61B 5/04012; A61B 5/04525; A61B 5/282; A61B 5/7264; G16H 50/20
See application file for complete search history.

(56) References Cited

U.S. PATENT DOCUMENTS 5,050,612 A * 9/1991 Matsumura ............. A61B 5/01
600/483
8,923,957 B2 * 12/2014 Yuk ..................... G06K 9/00536
600/509

(Continued)

OTHER PUBLICATIONS

Mathews et al. "A novel application of deep learning for single-lead ECG classification." Computers in Biology and Medicine, vol. 99, Aug. 1, 2018, pp. 53-62. (Year: 2018).*

(Continued)

*Primary Examiner* — Eric D. Bertram
(74) *Attorney, Agent, or Firm* — Brian J. Colandreo; Jeffrey T. Placker; Holland & Knight LLP (57) ABSTRACT

A computer-implemented method, computer program product and computing system for receiving a single-lead heartbeat waveform for a user; associating a heart health indicator with the single-lead heartbeat waveform; and providing the heart health indicator to a recipient.

27 Claims, 5 Drawing Sheets

(56) References Cited

U.S. PATENT DOCUMENTS

| | | | | |
|---|---|---|---|---|
| 9,693,711 | B2* | 7/2017 | Yuen | G06F 3/017 |
| 9,918,664 | B2* | 3/2018 | Blahnik | G06F 19/3481 |
| 9,999,744 | B2* | 6/2018 | Proud | A61M 21/02 |
| 10,272,294 | B2* | 4/2019 | Williams | G06T 11/60 |
| 10,503,268 | B2* | 12/2019 | Yuen | G06F 21/32 |
| 2005/0015115 | A1* | 1/2005 | Sullivan | A61B 5/4824 |
| | | | | 607/5 |
| 2005/0085736 | A1* | 4/2005 | Ambrose | A61B 5/061 |
| | | | | 600/509 |
| 2009/0281441 | A1* | 11/2009 | Zhang | A61B 5/0468 |
| | | | | 600/516 |
| 2010/0113950 | A1* | 5/2010 | Lin | A61B 5/02438 |
| | | | | 600/509 |
| 2015/0005650 | A1* | 1/2015 | Banet | A61B 5/046 |
| | | | | 600/509 |
| 2015/0018660 | A1* | 1/2015 | Thomson | A61B 5/332 |
| | | | | 600/393 |
| 2015/0257647 | A1* | 9/2015 | Buck | A61B 5/0028 |
| | | | | 600/388 |
| 2015/0366518 | A1* | 12/2015 | Sampson | A61B 5/7264 |
| | | | | 600/301 |
| 2016/0045167 | A1 | 2/2016 | Gheeraert et al. | |
| 2016/0135706 | A1* | 5/2016 | Sullivan | A61N 1/0484 |
| | | | | 600/301 |
| 2017/0281277 | A1* | 10/2017 | Gregg | A61B 5/7203 |
| 2018/0296105 | A1* | 10/2018 | Blake | A61B 5/0245 |
| 2018/0333063 | A1* | 11/2018 | Muchhala | G01R 33/0354 |
| 2019/0272920 | A1* | 9/2019 | Teplitzky | G06N 3/0454 |
| 2019/0336020 | A1* | 11/2019 | Kranz | A61B 5/0402 |
| 2020/0100693 | A1* | 4/2020 | Velo | A61B 5/681 |

OTHER PUBLICATIONS

Non-Final Office Action issued in U.S. Appl. No. 16/654,970 dated Dec. 17, 2019.

Final Office Action issued in related U.S. Appl. No. 16/654,979 dated May 7, 2020.

Non-Final Office Action issued in related U.S. Appl. No. 16/854,970 dated July 8, 2020.

Final Office Action issued in related U.S. Appl. No. 16/654,970 dated Nov. 30, 2020.

Non-Final Office Action issued in U.S. Appl. No. 16/654,854 dated May 4, 2021.

Non-Final Office Action issued in U.S. Appl. No. 16/654,970 dated Jun. 9, 2021.

Final Office Action issued in related U.S. Appl. No. 16/654,854 dated Oct. 4, 2021.

* cited by examiner

HEART SIGNAL WAVEFORM PROCESSING SYSTEM AND METHOD

RELATED APPLICATION(S)

This application claims the benefit of U.S. Provisional Application No. 62/746,282, filed on 16 Oct. 2018, the entire contents of which are incorporated herein by reference.

TECHNICAL FIELD

This disclosure relates to waveform analysis and, more particularly, to heartbeat waveform analysis.

BACKGROUND

As is known in the art, a Myocardial Infarction (MI), also known as a heart attack, occurs when blood flow decreases or stops to a part of the heart, causing damage to the heart muscle. The most common symptom is chest pain or discomfort, which may travel into the shoulder, arm, back, neck or jaw. Often this pain occurs in the center or left side of the chest and lasts for more than a few minutes. The discomfort may occasionally feel like heartburn. Other symptoms may include shortness of breath, nausea, feeling faint, a cold sweat or feeling tired.

About 30% of people have atypical symptoms, wherein women more often present without chest pain and instead have neck pain, arm pain or feel tired. Among those over 75 years old, about 5% have had an Myocardial Infarction with little or no history of symptoms. A Myocardial Infarction may cause heart failure, an irregular heartbeat, cardiogenic shock or cardiac arrest. Unfortunately, if the above-described symptoms are not recognized and treatment is not sought in a timely matter (e.g., less than 90 minutes), permanent damage to the heart muscle or death may occur.

SUMMARY OF DISCLOSURE

Concept 1

In one implementation, a computer-implemented method is executed on a computing system and includes: receiving a single-lead heartbeat waveform for a user; associating a heart health indicator with the single-lead heartbeat waveform; and providing the heart health indicator to a recipient.

One or more of the following features may be included. Associating a heart health indicator with the single-lead heartbeat waveform may include comparing one or more portions of the single-lead heartbeat waveform to one or more waveform features. Comparing one or more portions of the single-lead heartbeat waveform to one or more waveform features may include comparing an ST segment portion of the single-lead heartbeat waveform to one or more ST segment waveform features. Receiving a single-lead heartbeat waveform may include receiving the single-lead heartbeat waveform from an external device. The single-lead heartbeat waveform may be obtained via a differential voltage potential measurement concerning the heart of the user. The differential voltage potential measurement concerning the heart of the user may be obtained via a first electrode configured to be touched by a first appendage of the user and a second electrode configured to be touched by a second appendage of the user. The heart health indicator may be configured to indicate whether the user is having a heart attack. The recipient of the heart health indicator may be the user. The recipient of the heart health indicator may be a third party. Associating a heart health indicator with the single-lead heartbeat waveform may include: providing the single-lead heartbeat waveform to an external computing environment; utilizing the external computing environment to associate the heart health indicator with the single-lead heartbeat waveform; and receiving the heart health indicator from the external computing environment.

In another implementation, a computer program product resides on a computer readable medium and has a plurality of instructions stored on it. When executed by a processor, the instructions cause the processor to perform operations including: receiving a single-lead heartbeat waveform for a user; associating a heart health indicator with the single-lead heartbeat waveform; and providing the heart health indicator to a recipient.

One or more of the following features may be included. Associating a heart health indicator with the single-lead heartbeat waveform may include comparing one or more portions of the single-lead heartbeat waveform to one or more waveform features. Comparing one or more portions of the single-lead heartbeat waveform to one or more waveform features may include comparing an ST segment portion of the single-lead heartbeat waveform to one or more ST segment waveform features. Receiving a single-lead heartbeat waveform may include receiving the single-lead heartbeat waveform from an external device. The single-lead heartbeat waveform may be obtained via a differential voltage potential measurement concerning the heart of the user. The differential voltage potential measurement concerning the heart of the user may be obtained via a first electrode configured to be touched by a first appendage of the user and a second electrode configured to be touched by a second appendage of the user. The heart health indicator may be configured to indicate whether the user is having a heart attack. The recipient of the heart health indicator may be the user. The recipient of the heart health indicator may be a third party. Associating a heart health indicator with the single-lead heartbeat waveform may include: providing the single-lead heartbeat waveform to an external computing environment; utilizing the external computing environment to associate the heart health indicator with the single-lead heartbeat waveform; and receiving the heart health indicator from the external computing environment.

In another implementation, a computing system includes a processor and memory is configured to perform operations including: receiving a single-lead heartbeat waveform for a user; associating a heart health indicator with the single-lead heartbeat waveform; and providing the heart health indicator to a recipient.

One or more of the following features may be included. Associating a heart health indicator with the single-lead heartbeat waveform may include comparing one or more portions of the single-lead heartbeat waveform to one or more waveform features. Comparing one or more portions of the single-lead heartbeat waveform to one or more waveform features may include comparing an ST segment portion of the single-lead heartbeat waveform to one or more ST segment waveform features. Receiving a single-lead heartbeat waveform may include receiving the single-lead heartbeat waveform from an external device. The single-lead heartbeat waveform may be obtained via a differential voltage potential measurement concerning the heart of the user. The differential voltage potential measurement concerning the heart of the user may be obtained via a first electrode configured to be touched by a first appendage of the user and a second electrode configured to be touched by a second appendage of the user. The heart health indicator may be configured to indicate whether the user is having a heart attack. The recipient of the heart health indicator may be the user. The recipient of the heart health indicator may be a third party. Associating a heart health indicator with the single-lead heartbeat waveform may include: providing the single-lead heartbeat waveform to an external computing environment; utilizing the external computing environment to associate the heart health indicator with the single-lead heartbeat waveform; and receiving the heart health indicator from the external computing environment.

The details of one or more implementations are set forth in the accompanying drawings and the description below. Other features and advantages will become apparent from the description, the drawings, and the claims.

DETAILED DESCRIPTION OF THE PREFERRED EMBODIMENTS

System Overview

Figure 1:
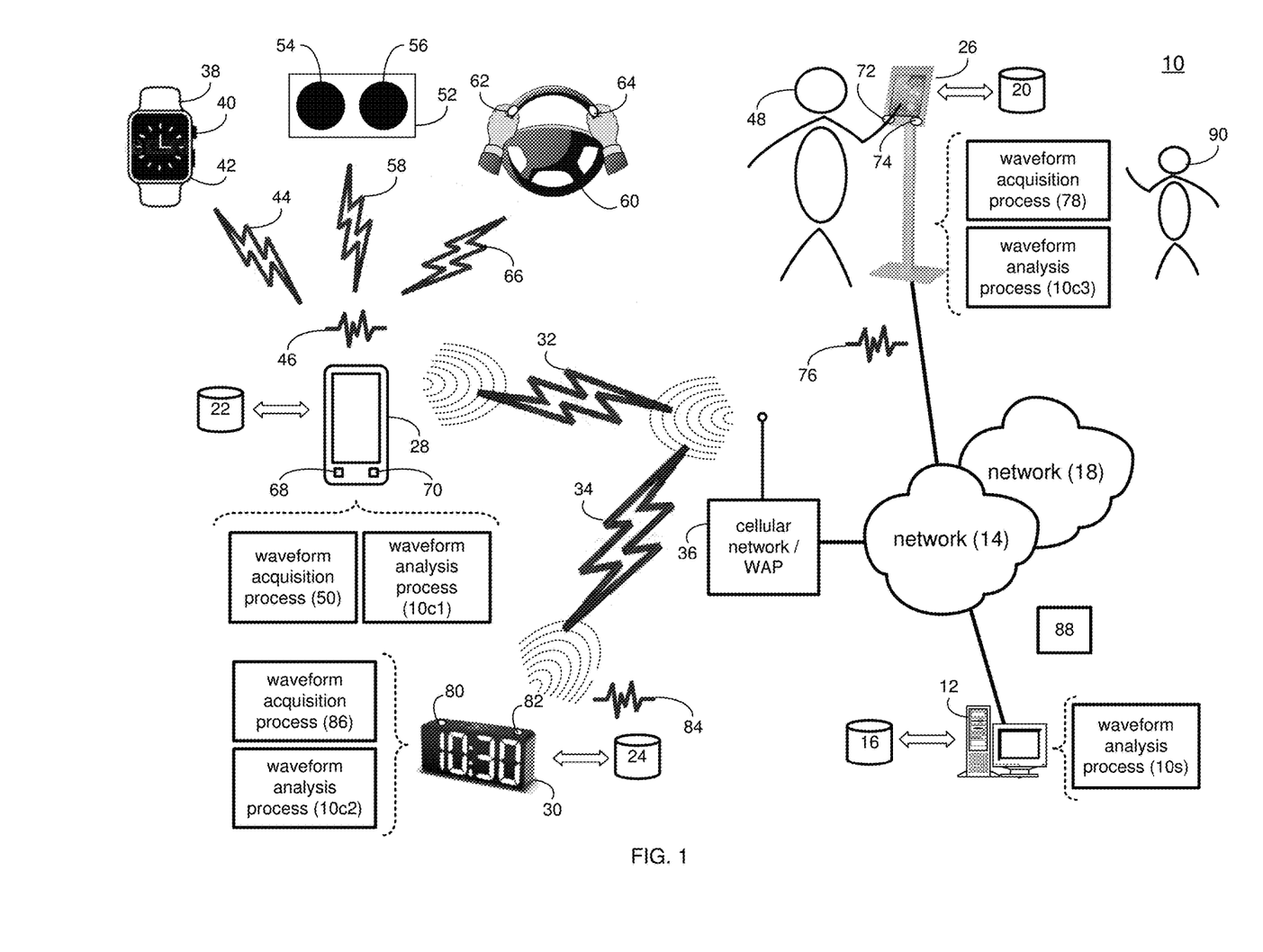
FIG. 1 is a diagrammatic view of a distributed computing network including a computing device that executes a waveform analysis process according to an embodiment of the present disclosure.

Referring to FIG. 1, there is shown waveform analysis process 10. Waveform analysis process 10 may be implemented as a server-side process, a client-side process, or a hybrid server-side/client-side process. For example, waveform analysis process 10 may be implemented as a purely server-side process via waveform analysis process 10s. Alternatively, waveform analysis process 10 may be implemented as a purely client-side process via one or more of waveform analysis process 10c1, waveform analysis process 10c2, and waveform analysis process 10c3. Alternatively still, waveform analysis process 10 may be implemented as a hybrid server-side/client-side process via waveform analysis process 10s in combination with one or more of waveform analysis process 10c1, waveform analysis process 10c2, and waveform analysis process 10c3. Accordingly, waveform analysis process 10 as used in this disclosure may include any combination of waveform analysis process 10s, waveform analysis process 10c1, waveform analysis process 10c2 and waveform analysis process 10c3.

Waveform analysis process 10s may be a server application and may reside on and may be executed by computing device 12, which may be connected to network 14 (e.g., the Internet or a local area network). Examples of computing device 12 may include, but are not limited to: a personal computer, a laptop computer, a personal digital assistant, a data-enabled cellular telephone, a notebook computer, a television with one or more processors embedded therein or coupled thereto, a cable/satellite receiver with one or more processors embedded therein or coupled thereto, a server computer, a series of server computers, a mini computer, a mainframe computer, or a cloud-based computing platform.

The instruction sets and subroutines of waveform analysis process 10s, which may be stored on storage device 16 coupled to computing device 12, may be executed by one or more processors (not shown) and one or more memory architectures (not shown) included within computing device 12. Examples of storage device 16 may include but are not limited to: a hard disk drive; a RAID device; a random access memory (RAM); a read-only memory (ROM); and all forms of flash memory storage devices.

Network 14 may be connected to one or more secondary networks (e.g., network 18), examples of which may include but are not limited to: a local area network; a wide area network; or an intranet, for example.

Examples of waveform analysis processes 10c1, 10c2, 10c3 may include but are not limited to a client application, a web browser, an embedded application within a consumer electronic device, or a specialized application (e.g., an application running on e.g., the Android™ platform or the iOS™ platform). The instruction sets and subroutines of waveform analysis processes 10c1, 10c2, 10c3, which may be stored on storage devices 20, 22, 24 (respectively) coupled to client electronic devices 26, 28, 30 (respectively), may be executed by one or more processors (not shown) and one or more memory architectures (not shown) incorporated into client electronic devices 26, 28, 30 (respectively). Examples of storage devices 20, 22, 24 may include but are not limited to: a hard disk drive; a RAID device; a random access memory (RAM); a read-only memory (ROM); and all forms of flash memory storage devices.

Examples of client electronic devices 26, 28, 30 may include, but are not limited to: waveform analysis kiosk 26 (e.g., which may be placed within pharmaceutical stores, shopping malls, medical care facilities, places of public gathering, etc.), smart handheld device 28 (e.g., smart telephones, personal digital assistants, etc.), connected device 30 (e.g., smart clocks, Amazon assistants, Google assistants, etc.), a laptop computer (not shown), a piece of exercise equipment (e.g., a treadmill or an elliptical; not shown) and a dedicated network device (not shown). Client electronic devices 26, 28, 30 may each execute an operating system, examples of which may include but are not limited to Microsoft Windows™, Android™, WebOS™, iOS™, Redhat Linux™, or a custom operating system.

Users of client electronic devices 26, 28, 30 may access waveform analysis process 10 directly through network 14 or through secondary network 18. Further, waveform analysis process 10 may be connected to network 14 through secondary network 18.

The various client electronic devices (e.g., client electronic devices 26, 28, 30) may be directly or indirectly coupled to network 14 (or network 18). For example, smart handheld device 28 and connected device 30 are shown wirelessly coupled to network 14 via wireless communication channels 32, 34 (respectively) established between smart handheld device 28 and connected device 30 (respectively) and cellular network/WAP 36, which is shown directly coupled to network 14. Additionally, waveform analysis kiosk 26 is shown directly coupled to network 14 via a hardwired network connection.

The WAP portion of cellular network/WAP 36 may be, for example, an IEEE 802.11a, 802.11b, 802.11g, 802.11n, Wi-Fi, and/or Bluetooth device that is capable of establishing wireless communication channels 32, 34 between smart handheld device 28, connected device 30 (respectively) and the WAP portion of cellular network/WAP 36. As is known in the art, IEEE 802.11x specifications may use Ethernet protocol and carrier sense multiple access with collision avoidance (i.e., CSMA/CA) for path sharing. As is known in the art, Bluetooth is a telecommunications industry specification that allows e.g., mobile phones, computers, and personal digital assistants to be interconnected using a short-range wireless connection.

For example, smart watch 38 (e.g., an Apple Watch™ or a Fitbit™ that includes electrodes 40, 42 configured to form electrical connections with e.g., two fingers on opposite hands of a user) may be configured to be wirelessly coupled to smart handheld device 28 via wireless communication channel 44 (e.g., a Bluetooth communication channel or an ultrasound communication channel), wherein smart watch 38 may be configured to acquire heartbeat waveform 46 from a wearer (e.g., user 48) of smart watch 38 via waveform acquisition process 50.

Additionally, touchpad device 52 (e.g., a dedicated device that includes electrodes 54, 56 configured to form electrical connections with e.g., two fingers on opposite hands of a user) may be configured to be wirelessly coupled to smart handheld device 28 via wireless communication channel 58 (e.g., a Bluetooth communication channel or an ultrasound communication channel), wherein touchpad device 52 may be configured to acquire heartbeat waveform 46 from a user (e.g., user 48) of touchpad device 52 via waveform acquisition process 50.

Additionally still, steering wheel 60 (e.g., a vehicle steering wheel that includes electrodes 62, 64 configured to form electrical connections with e.g., two fingers on opposite hands of a user) may be configured to be wirelessly coupled to smart handheld device 28 via wireless communication channel 66 (e.g., a Bluetooth communication channel or an ultrasound communication channel), wherein steering wheel 60 may be configured to acquire heartbeat waveform 46 from a user (e.g., user 48) of steering wheel 60 via waveform acquisition process 50.

Further, smart handheld device 28 may include electrodes 68, 70 configured to form electrical connections with e.g., two fingers on opposite hands of a user, thus enabling smart handheld device 28 to directly acquire heartbeat waveform 46 from a user (e.g., user 48) of smart handheld device 28 via waveform acquisition process 50 (i.e., without the need for smart watch 38, touchpad device 52 or steering wheel 60)

Waveform analysis kiosk 26 may include electrodes 72, 74 configured to form electrical connections with e.g., two fingers on opposite hands of a user, thus enabling waveform analysis kiosk 26 to directly acquire heartbeat waveform 76 from a user (e.g., user 48) of waveform analysis kiosk 26 via waveform acquisition process 78.

Connected device 30 may include electrodes 80, 82 configured to form electrical connections with e.g., two fingers on opposite hands of a user, thus enabling connected device 30 to directly acquire heartbeat waveform 84 from a user (e.g., user 48) of connected device 30 via waveform acquisition process 86.

Heartbeat Waveform

Figure 2:
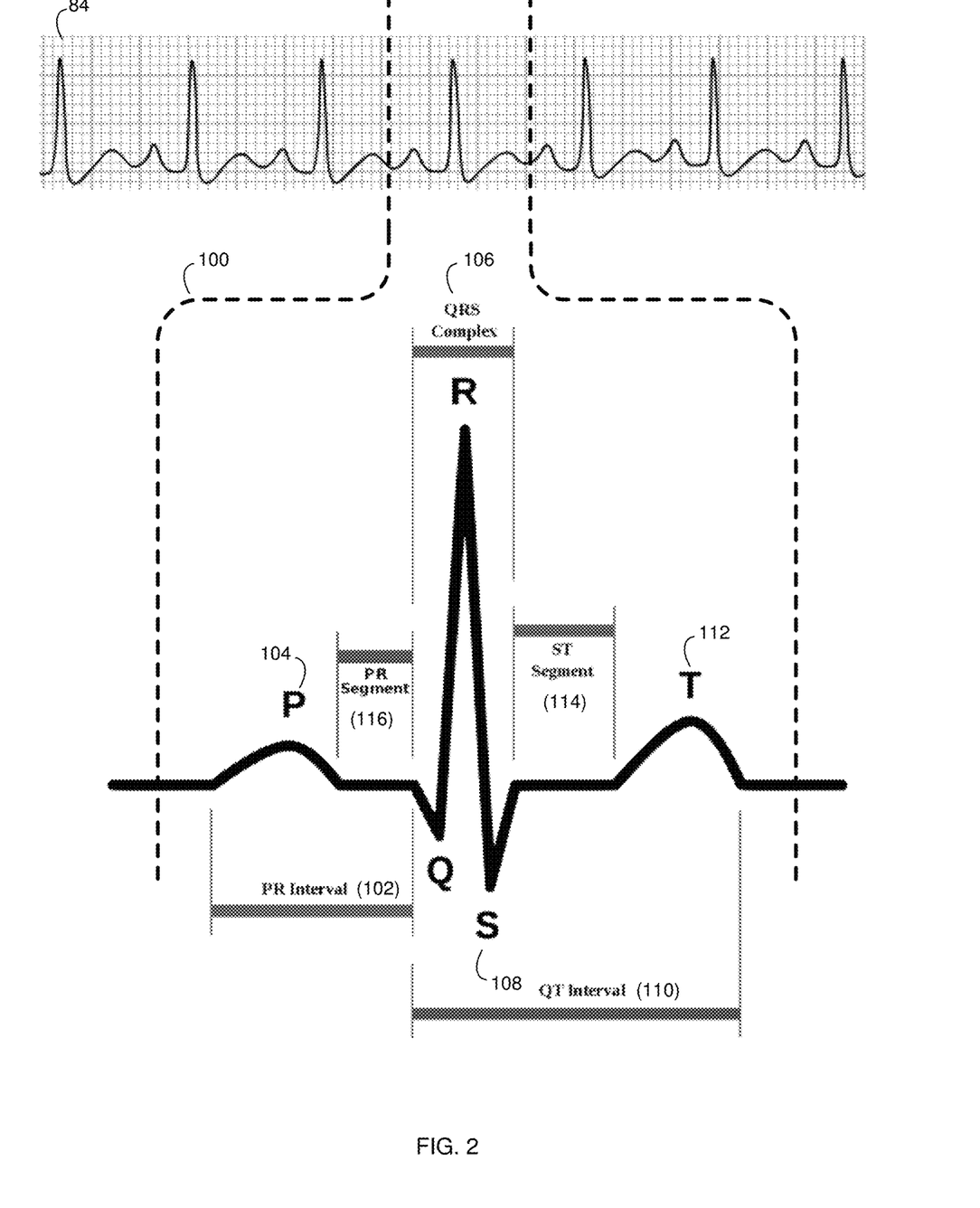
FIG. 2 is a diagrammatic view of the type of heartbeat waveform that may be processed by the waveform analysis process of FIG. 1 according to an embodiment of the present disclosure.

Referring also to FIG. 2 and as will be discussed below in greater detail, there is shown one example of heartbeat waveform 84 (i.e., a voltage versus time representation of the electrical activity of a beating heart) in normal sinus rhythm. As is known in the art, a sinus rhythm is any cardiac rhythm in which depolarization of the cardiac muscle begins at the sinus node. It is characterized by the presence of correctly oriented P waves on the electrocardiogram (ECG). Sinus rhythm is necessary, but not sufficient, for normal electrical activity within the heart.

Letters (PQRST) are used to indicate important points within one cycle of heartbeat waveform 84. PR Interval portion 102 indicates atrioventricular conduction time, wherein PR Interval portion 102 is measured from where the P wave (i.e., point 104) begins until the beginning of QRS complex portion 106. QRS complex portion 106 indicates ventricular depolarization, wherein QRS complex portion 106 is measured from the end of PR interval portion 102 to the end of the S wave (i.e., point 108). QT interval portion 110 indicates ventricular activity (i.e., both depolarization and repolarization), wherein QT interval portion 110 is measured from the beginning of QRS complex portion 106 to the end of the T wave (i.e., point 112). ST segment portion 114 traces the early part of ventricular repolarization, wherein ST segment portion 114 begins at the end of QRS complex portion 106 and continues to the beginning of the T wave (i.e., point 112). PR segment portion 116 may indicate certain cardiac disease states (e.g., pericarditis or atrial infarction), wherein PR segment portion 116 is measured from the end of the P wave (i.e., point 104) to the beginning of QRS complex 106.

Waveform Analysis Process

As discussed above, waveform analysis kiosk 26 may be configured to receive heartbeat waveform 76. Further, smart handheld device 28 may be configured to receive heartbeat waveform 46. Additionally, connected device 30 may be configured to receive heartbeat waveform 84.

Further and as discussed above, heartbeat waveforms 46, 76, 84 may be obtained via pairs of electrodes (e.g., electrodes 40 & 42, electrodes 54 & 56, electrodes 62 & 64, electrodes 68 & 70, electrodes 72 & 74, and electrodes 80 & 82). Specifically, heartbeat waveforms 46, 76, 84 may be obtained via a first electrode (of an electrode pair) configured to be touched by a first appendage of the user (e.g., user 48) and a second electrode (of the electrode pair) configured to be touched by a second appendage of the user (e.g., user 48). For example, each of these electrode pairs may be configured to form electrical connections with e.g., two fingers on opposite hands of a user (e.g., user 48). Such a configuration may result in a differential voltage potential measurement concerning the heart of the user (e.g., user 48) and, therefore, heartbeat waveforms 46, 76, 84 may be single-lead (i.e., single voltage potential) heartbeat waveforms. While the pairs of electrodes (e.g., electrodes 40 & 42, electrodes 54 & 56, electrodes 62 & 64, electrodes 68 & 70, electrodes 72 & 74, and electrodes 80 & 82) are described above as being incorporated into various electronic devices (e.g., smart watch 38, touchpad device 52, steering wheel 60, waveform analysis kiosk 26 and connected device 30, respectively), this is for illustrative purposes only and is not intended to be a limitation of this disclosure, as other configurations are possible and are considered to be within the scope of this disclosure. For example, the "pair of electrodes" may be a pair of traditional "peel and stick" electrocardiogram electrodes (not shown) that may be affixed to a user's chest and plugged into a bedside monitor (not shown), an ICU monitor (not shown), a multi-parameter monitor (not shown) and automated external defibrillator (not shown).

Figure 3:
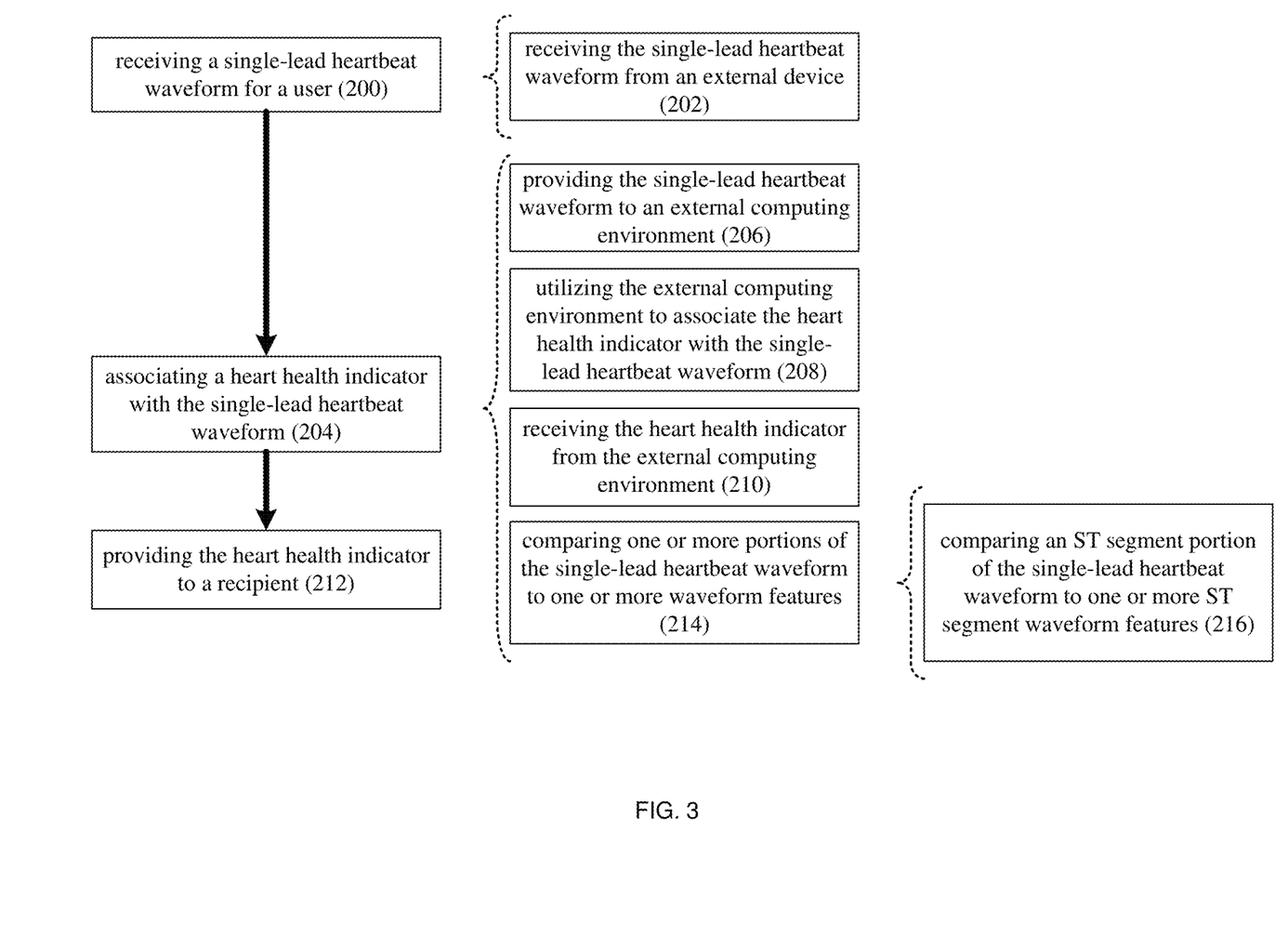
FIG. 3 is a flowchart of an implementation of the waveform analysis process of FIG. 1 according to an embodiment of the present disclosure.

Referring also to FIG. 3, waveform analysis process 10 may receive 200 a single-lead heartbeat waveform (e.g., one of heartbeat waveforms 46, 76, 84) for a user (e.g., user 48). When receiving 200 the single-lead heartbeat waveform (e.g., one of heartbeat waveforms 46, 76, 84), waveform analysis process 10 may receive 202 the single-lead heartbeat waveform (e.g., one of heartbeat waveforms 46, 76, 84) from an external device.

For example and as discussed above, smart handheld device 28 may receive 202 heartbeat waveform 46 from e.g., smart watch 38, touchpad device 52, or steering wheel 60, wherein smart watch 38, touchpad device 52, and steering wheel 60 may include a pair of electrodes that enable the acquisition of heartbeat waveform 46 via waveform acquisition process 50. Such a waveform acquisition process and an electrode pair may be natively included in such external devices. For example, the current version of the Apple Watch™ includes such a waveform acquisition process (e.g., waveform acquisition process 50) and such an electrode pair (e.g., electrodes 40, 42), wherein such smart watches may monitor the heart rhythm of the wearer and e.g., notify the wearer if their heart rate remains above or below a chosen beats per minute (BPM) or if an irregular heart rhythm (e.g., AFib) is detected.

Alternatively, the single-lead heartbeat waveform (e.g., one of heartbeat waveforms 46, 76, 84) may be locally acquired. For example and as discussed above, smart handheld device 28 may include electrodes 68, 70 configured to form electrical connections with e.g., two fingers on opposite hands of a user, thus enabling smart handheld device 28 to directly acquire heartbeat waveform 46 from a user (e.g., user 48) of smart handheld device 28 via waveform acquisition process 50. Further and as discussed above, waveform analysis kiosk 26 may include electrodes 72, 74 configured to form electrical connections with e.g., two fingers on opposite hands of a user, thus enabling waveform analysis kiosk 26 to directly acquire heartbeat waveform 76 from a user (e.g., user 48) of waveform analysis kiosk 26 via waveform acquisition process 78. Additionally and as discussed above, connected device 30 may include electrodes 80, 82 configured to form electrical connections with e.g., two fingers on opposite hands of a user, thus enabling connected device 30 to directly acquire heartbeat waveform 84 from a user (e.g., user 48) of connected device 30 via waveform acquisition process 86

Regardless of the manner in which the single-lead heartbeat waveform (e.g., one of heartbeat waveforms 46, 76, 84) is acquired (e.g., from an external device or locally acquired), waveform analysis process 10 may associate 204 a heart health indicator (e.g., heart health indicator 88) with the single-lead heartbeat waveform (e.g., one of heartbeat waveforms 46, 76, 84). Examples of such a heart health indicator (e.g., heart health indicator 88) may include a text-based heart health indicator or an audio-based heart health indicator. When analyzing the single-lead heartbeat waveform (e.g., one of heartbeat waveforms 46, 76, 84), the quantity of individual heartbeats analyzed and/or the duration of the heartbeat waveform analyzed may vary depending upon the type of analysis being performed. For example, as little as a single heartbeat may be analyzed or an plurality of heartbeats spanning a longer duration (e.g., thirty seconds) may be analyzed.

This heart health indicator (e.g., heart health indicator 88) may be configured to indicate whether the user (e.g., user 46) is having a heart attack. As is known in the art, a heart attack happens when the flow of oxygen-rich blood in one or more of the coronary arteries (which supply the heart muscle) suddenly becomes blocked, and a section of heart muscle can no longer get enough oxygen. This blockage may occur when plaque ruptures. If blood flow is not restored quickly (either by medicine that dissolves the blockage or a catheter placed within the artery that physically opens the blockage), the section of heart muscle begins to die. Accordingly and in the event of the occurrence of a heart attack, the more quickly treatment is administered, the more likely it is that the sufferer will survive the heart attack. Therefore, quickly realizing that you are having a heart attack (as opposed to thinking that you are experiencing heartburn or indigestion) is of paramount importance.

For example, heart health indicator 88 may be a binary indicator configured to indicate whether the user (e.g., user 48) is having a heart attack. For example and if the single-lead heartbeat waveform (e.g., one of heartbeat waveforms 46, 76, 84) seems to be normal (i.e., no heart attack), heart health indicator 88 may be "You do not appear to be having a heart attack." However and if the single-lead heartbeat waveform (e.g., one of heartbeat waveforms 46, 76, 84) seems to be concerning (i.e., heart attack), heart health indicator 88 may be "You appear to be having a heart attack. Seek medical attention Immediately".

Alternatively, heart health indicator 88 need not be binary and may be a likelihood indicator configured to indicate whether the user (e.g., user 48) is having a heart attack. For example and if the single-lead heartbeat waveform (e.g., one of heartbeat waveforms 46, 76, 84) seems to be normal (i.e., no heart attack), heart health indicator 88 may be "There is an 84% probability that you are not having a heart attack." However and if the single-lead heartbeat waveform (e.g., one of heartbeat waveforms 46, 76, 84) seems to be concerning (i.e., heart attack), heart health indicator 88 may be "There is a 90% probability that you are having a heart attack. Seek medical attention Immediately".

In the event that the device (e.g., waveform analysis kiosk 26, smart handheld device 28, connected device 30) is capable of external communications, such a device (e.g., waveform analysis kiosk 26, smart handheld device 28, connected device 30) may offer to (or automatically) contact emergency medical services (e.g., 911 in the United States of America) in the event that the user (e.g., user 48) is having a heart attack. In the event that the device is capable of autonomous driving (e.g., steering wheel 60 is included within a vehicle having autonomous driving capabilities) and is capable of external communications, emergency medical services (e.g., 911 in the United States of America) may be contacted and the vehicle may autonomous drive to the closest hospital/trauma center in the event that the user (e.g., user 48) is having a heart attack.

Depending upon the manner in which the device (e.g., waveform analysis kiosk 26, smart handheld device 28, connected device 30) is configured, the process of associating 204 a heart health indicator (e.g., heart health indicator 88) with the single-lead heartbeat waveform (e.g., one of heartbeat waveforms 46, 76, 84) may be performed locally or remotely. For example, it is foreseeable that some of the devices (e.g., waveform analysis kiosk 26 and smart handheld device 28) may have more data processing capabilities; while other devices (e.g., smart watch 38 and connected device 30) may have less data processing capabilities.

Accordingly and for the devices (e.g., waveform analysis kiosk 26 and smart handheld device 28) that have more data processing capabilities, the process of associating 204 a heart health indicator (e.g., heart health indicator 88) with the single-lead heartbeat waveform (e.g., one of heartbeat waveforms 46, 76, 84) may be performed locally (as these devices have the processing capabilities required to accurately and timely process the single-lead heartbeat waveform (e.g., one of heartbeat waveforms 46, 76, 84).

Conversely and for the devices (e.g., smart watch 38 and connected device 30) that have less data processing capabilities, the process of associating 204 a heart health indicator (e.g., heart health indicator 88) with the single-lead heartbeat waveform (e.g., one of heartbeat waveforms 46, 76, 84) may be performed remotely (as these devices do not have the processing capabilities required to accurately and timely process the single-lead heartbeat waveform (e.g., one of heartbeat waveforms 46, 76, 84).

Specifically and in such a situation, when associating 204 a heart health indicator (e.g., heart health indicator 88) with the single-lead heartbeat waveform (e.g., one of heartbeat waveforms 46, 76, 84), waveform analysis process 10 may provide 206 the single-lead heartbeat waveform (e.g., one of heartbeat waveforms 46, 76, 84) to an external computing environment (e.g., computing device 12). As discussed above, examples of computing device 12 may include, but are not limited to: a personal computer, a laptop computer, a personal digital assistant, a data-enabled cellular telephone, a notebook computer, a television with one or more processors embedded therein or coupled thereto, a cable/satellite receiver with one or more processors embedded therein or coupled thereto, a server computer, a series of server computers, a mini computer, a mainframe computer, or a cloud-based computing platform.

Further and when associating 204 a heart health indicator (e.g., heart health indicator 88) with the single-lead heartbeat waveform (e.g., one of heartbeat waveforms 46, 76, 84), waveform analysis process 10 may utilize 208 the external computing environment (e.g., computing device 12) to associate the heart health indicator (e.g., heart health indicator 88) with the single-lead heartbeat waveform (e.g., one of heartbeat waveforms 46, 76, 84) and may receive 210 the heart health indicator (e.g., heart health indicator 88) from the external computing environment (e.g., computing device 12).

Once a heart health indicator (e.g., heart health indicator 88) is associated 204 with the single-lead heartbeat waveform (e.g., one of heartbeat waveforms 46, 76, 84), waveform analysis process 10 may provide 212 the heart health indicator (e.g., heart health indicator 88) to a recipient, wherein examples of such a recipient of the heart health indicator (e.g., heart health indicator 88) may include but are not limited to the user (e.g., user 48) or a third party (e.g., a medical professional working at a hospital in which waveform analysis kiosk 26 is deployed).

Figure 4:
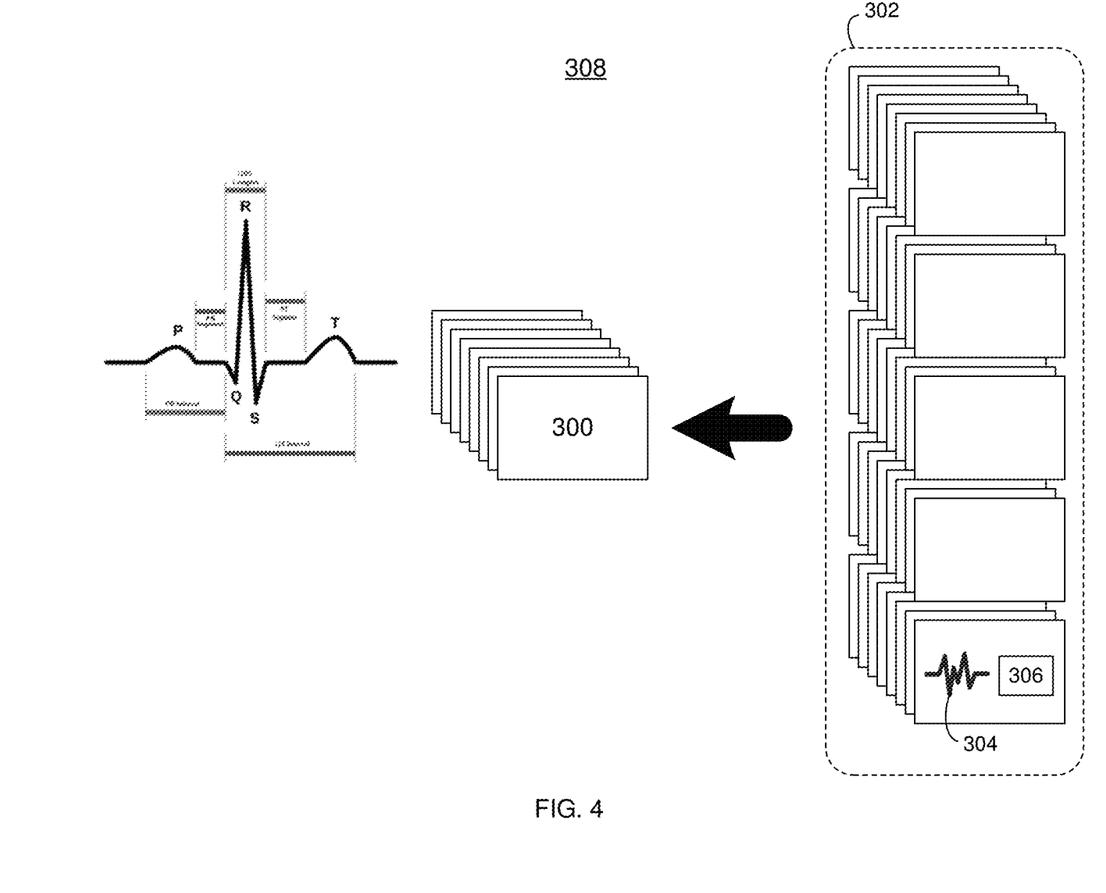
FIG. 4 is a diagrammatic view of a plurality of specimen waveform records and the waveform features derived therefrom by the waveform analysis process of FIG. 1 according to an embodiment of the present disclosure.

Referring also to FIG. 4, when associating 204 a heart health indicator (e.g., heart health indicator 88) with the single-lead heartbeat waveform (e.g., one of heartbeat waveforms 46, 76, 84), waveform analysis process 10 may compare 214 one or more portions (e.g., the PR Interval portion, the QRS complex portion, the QT interval portion, the ST segment portion, and the PR segment portion) of the single-lead heartbeat waveform (e.g., one of heartbeat waveforms 46, 76, 84) to one or more waveform features (e.g., waveform features 300), wherein waveform features 300 may be essentially waveform rules derived from a plurality of specimen waveform records (e.g., specimen waveform records 302).

These waveform features (e.g., waveform features 300) may be generated via ML (i.e., Machine Learning) and therefore may be ML-generated waveform features. For example, the one or more waveform features (e.g., waveform features 300) may be generated by processing a plurality of specimen waveform records (e.g., specimen waveform records 302), wherein each of the specimen waveform records (e.g., specimen waveform records 302) may include a specimen heartbeat waveform (e.g., specimen heartbeat waveform 304) and a related clinical heart health diagnosis (e.g., clinical heart health diagnosis 306). At least a portion of the plurality of specimen waveform records (e.g., specimen waveform records 302) may include a specimen heartbeat waveform (e.g., specimen heartbeat waveform 304) that was generated via a conventional 12-lead electrocardiogram. An example of such a related clinical heart health diagnosis (e.g., clinical heart health diagnosis 306) may include but is not limited to whether the patient associated with the particular specimen waveform record had suffered a heart attack.

For example, specimen waveform records 302 may be a massive data set and may include millions of waveform records that are processed using machine learning/artificial intelligence and probabilistic modelling. Assume that waveform analysis process 10 is configured to process content (e.g., specimen waveform records 302), wherein examples of specimen waveform records 302 may include but are not limited to unstructured content and structured content.

As is known in the art, structured content may be content that is separated into independent portions (e.g., fields, columns, features) and, therefore, may have a pre-defined data model and/or is organized in a pre-defined manner. For example, if the structured content concerns an employee list: a first field, column or feature may define the first name of the employee; a second field, column or feature may define the last name of the employee; a third field, column or feature may define the home address of the employee; and a fourth field, column or feature may define the hire date of the employee.

Further and as is known in the art, unstructured content may be content that is not separated into independent portions (e.g., fields, columns, features) and, therefore, may not have a pre-defined data model and/or is not organized in a pre-defined manner. For example, if the unstructured content concerns the same employee list: the first name of the employee, the last name of the employee, the home address of the employee, and the hire date of the employee may all be combined into one field, column or feature.

For the following example, assume that specimen waveform records 302 are structured content, wherein each of the specimen waveform records (e.g., specimen waveform records 302) includes a specimen heartbeat waveform (e.g., specimen heartbeat waveform 304) and a related clinical heart health diagnosis (e.g., clinical heart health diagnosis 306).

When processing content (e.g., specimen waveform records 302), waveform analysis process 10 may use probabilistic modeling to accomplish such processing, wherein examples of such probabilistic modeling may include but are not limited to discriminative modeling, generative modeling, or combinations thereof.

As is known in the art, probabilistic modeling may be used within modern artificial intelligence systems (e.g., waveform analysis process 10), in that these probabilistic models may provide artificial intelligence systems with the tools required to autonomously analyze vast quantities of data (e.g., specimen waveform records 302).

Examples of the tasks for which probabilistic modeling may be utilized may include but are not limited to:
  predicting media (music, movies, books) that a user may like or enjoy based upon media that the user has liked or enjoyed in the past;
  transcribing words spoken by a user into editable text;
  grouping genes into gene clusters;
  identifying recurring patterns within vast data sets;

filtering email that is believed to be spam from a user's inbox;

generating clean (i.e., non-noisy) data from a noisy data set;

analyzing (voice-based or text-based) customer feedback; and diagnosing various medical conditions and diseases.

For each of the above-described applications of probabilistic modeling, an initial probabilistic model may be defined, wherein this initial probabilistic model may be subsequently (e.g., iteratively or continuously) modified and revised, thus allowing the probabilistic models and the artificial intelligence systems (e.g., waveform analysis process 10) to "learn" so that future probabilistic models may be more precise and may explain more complex data sets.

Specifically, each specimen heartbeat waveform (e.g., specimen heartbeat waveform 304) may include a plurality of discrete waveform portions. For example and as discussed above, each specimen heartbeat waveform (e.g., specimen heartbeat waveform 304) may include:

- a PR Interval portion that indicates atrioventricular conduction time;
- a QRS complex portion that indicates ventricular depolarization;
- a QT interval portion that indicates ventricular activity (i.e., both depolarization and repolarization);
- an ST segment portion that traces the early part of ventricular repolarization; and
- a PR segment portion that may indicate certain cardiac disease states (e.g., pericarditis or atrial infarction).

As discussed above, an example of such a related clinical heart health diagnosis (e.g., clinical heart health diagnosis 306) may include but is not limited to whether the patient associated with the particular specimen waveform record had suffered a heart attack.

Accordingly and through use of the above-described machine learning, artificial intelligence and probabilistic modelling, waveform analysis process 10 may associate at least one of the plurality of discrete waveform portions (e.g., the PR Interval portion, the QRS complex portion, the QT interval portion, the ST segment portion, and the PR segment portion) with the related clinical heart health diagnosis (e.g., whether or not the patient associated with the particular specimen waveform record had suffered a heart attack).

As discussed above, ST segment portion 114 traces the early part of ventricular repolarization, wherein ST segment portion 114 begins at the end of QRS complex portion 106 and continues to the beginning of the T wave (i.e., point 112). As is known in the art, if ST segment portion 114 is elevated, the user may be experiencing a ST-segment elevation myocardial infarction (STEMI), wherein a STEMI is a serious form of heart attack in which a coronary artery is completely blocked and a large part of the heart muscle is unable to receive blood.

Accordingly and when comparing 214 one or more portions (e.g., the PR Interval portion, the QRS complex portion, the QT interval portion, the ST segment portion, and the PR segment portion) of the single-lead heartbeat waveform (e.g., one of heartbeat waveforms 46, 76, 84) to one or more waveform features (e.g., waveform features 300), waveform analysis process 10 may compare 216 an ST segment portion (e.g., ST segment portion 114) of the single-lead heartbeat waveform (e.g., one of heartbeat waveforms 46, 76, 84) to one or more ST segment waveform features (e.g., included within waveform features 300) to e.g., determine if the ST segment portion of the single-lead heartbeat waveform (e.g., one of heartbeat waveforms 46, 76, 84) is elevated (which may be indicative of user 48 having a heart attack).

As each of the above-described specimen waveform records (e.g., specimen waveform records 302) includes a specimen heartbeat waveform (e.g., specimen heartbeat waveform 304) and a related clinical heart health diagnosis (e.g., clinical heart health diagnosis 306), the above-described machine learning, artificial intelligence and probabilistic modelling may be utilized to examine each specimen heartbeat waveform (e.g., specimen heartbeat waveform 304) and its related clinical heart health diagnosis (e.g., clinical heart health diagnosis 306) to determine e.g., just how much an ST segment portion needs to be elevated in order for the user to be considered having a heart attack. Or what particular type/shape/duration of ST segment portion elevation is indicative of a heart attack. Or if the elevation of any other portions of a specimen heartbeat waveform (alone or when coupled with an elevation of an ST segment portion of a specimen heartbeat waveform) increases (or decreases) the likelihood that a user is having a heart attack.

Accordingly and since the above-described specimen waveform records (e.g., specimen waveform records 302) includes a specimen heartbeat waveform (e.g., specimen heartbeat waveform 304) and its related clinical heart health diagnosis (e.g., clinical heart health diagnosis 306), the above-described machine learning, artificial intelligence and probabilistic modelling may be utilized to examine each specimen heartbeat waveform (e.g., specimen heartbeat waveform 304) and its related clinical heart health diagnosis (e.g., clinical heart health diagnosis 306) to generate waveform features 300, wherein waveform features 300 may be essentially waveform rules derived through the above-described machine learning, artificial intelligence and probabilistic modelling.

For example and for illustrative purposes only, waveform analysis process 10 may observe that:

- a patient was diagnosed with a heart attack 90% of the time when Portion X of a specimen heartbeat waveform was elevated by more than 50%;
- a patient was diagnosed with a heart attack 95% of the time when Portion X of a specimen heartbeat waveform was elevated by more than 50% and Portion Y of a specimen heartbeat waveform was elevated by more than 30%;
- a patient was diagnosed with a heart attack 100% of the time when Portion X of a specimen heartbeat waveform was elevated by more than 75% and Portion Y of a specimen heartbeat waveform was elevated by more than 50%; and
- a patient was diagnosed with a heart attack 0% of the time when Portion X of a specimen heartbeat waveform was elevated by less than 5%.

According and through the use of such observations, waveform analysis process 10 may derive waveform features 300 (e.g., waveform rules). This combination of waveform features 300 and specimen waveform records 302 may form machine-readable dataset 308 (which may be configured to be accessed/utilized by third parties).

ML-Generated Data Set

Accordingly, machine-readable dataset 308 may include: a plurality of specimen waveform records (e.g., specimen waveform records 302), wherein each specimen waveform record includes a specimen heartbeat waveform (e.g., specimen heartbeat waveform 304) and a related clinical heart health diagnosis (e.g., clinical heart health diagnosis 306). Each specimen heartbeat waveform (e.g., specimen heartbeat waveform 304) may include a plurality of discrete waveform portions (e.g., the PR Interval portion, the QRS complex portion, the QT interval portion, the ST segment portion, and the PR segment portion). At least one association may be made that associates at least one of the plurality of discrete waveform portions (e.g., the PR Interval portion, the QRS complex portion, the QT interval portion, the ST segment portion, and the PR segment portion) of each specimen heartbeat waveform with the related clinical heart health diagnosis. For example, Portion A of a first patient's specimen heartbeat waveform was elevated by over 50% and they had a heart attack; Portion A of a second patient's specimen heartbeat waveform was elevated by less than 20% and they did not have a heart attack; Portion B of a third patient's specimen heartbeat waveform was elevated by over 80% and they had a heart attack; and Portion B of a fourth patient's specimen heartbeat waveform was elevated by less than 40% and they did not have a heart attack.

Generating the Data Set

Figure 5:
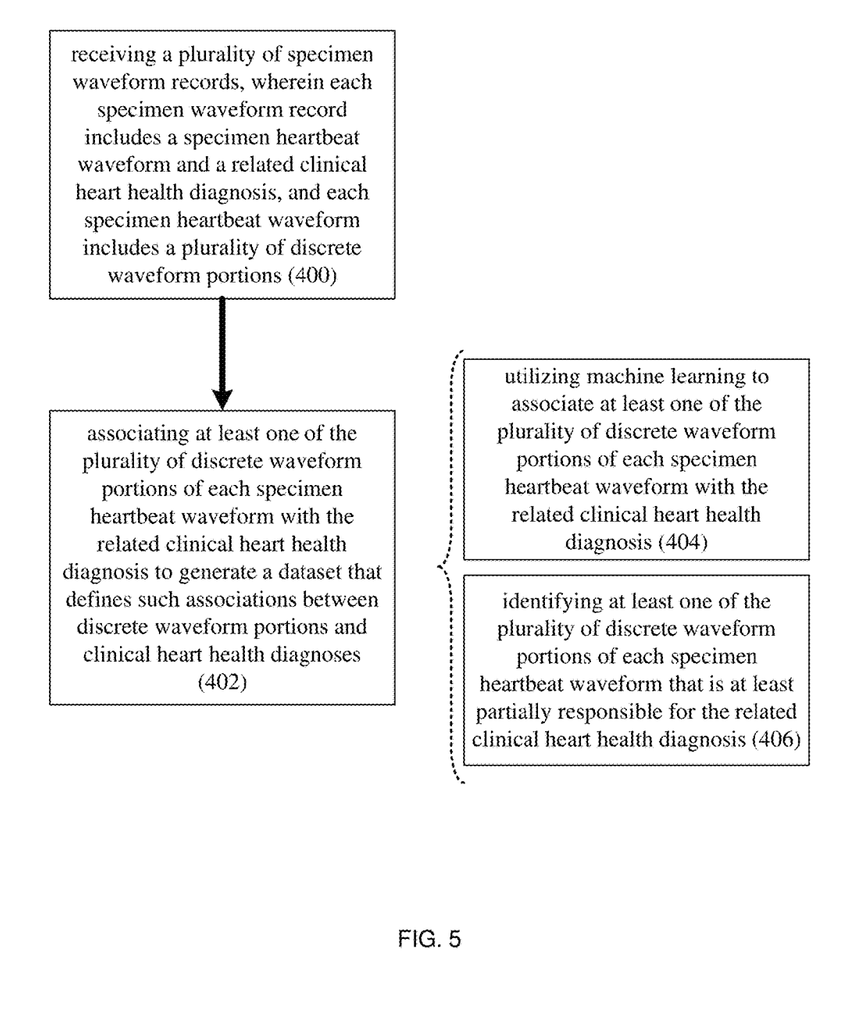
FIG. 5 is a flowchart of another implementation of the waveform analysis process of FIG. 1 according to an embodiment of the present disclosure; and Like reference symbols in the various drawings indicate like elements.

Referring also to FIG. 5 and when generating machine-readable dataset 308, waveform analysis process 10 may receive 400 a plurality of specimen waveform records (e.g., specimen waveform records 302), wherein each specimen waveform record includes a specimen heartbeat waveform (e.g., specimen heartbeat waveform 304) and a related clinical heart health diagnosis (e.g., clinical heart health diagnosis 306). As discussed above, each specimen heartbeat waveform (e.g., specimen heartbeat waveform 304) may include a plurality of discrete waveform portions (e.g., the PR Interval portion, the QRS complex portion, the QT interval portion, the ST segment portion, and the PR segment portion).

Waveform analysis process 10 may associate 402 at least one of the plurality of discrete waveform portions (e.g., the PR Interval portion, the QRS complex portion, the QT interval portion, the ST segment portion, and the PR segment portion) of each specimen heartbeat waveform (e.g., specimen heartbeat waveform 304) with the related clinical heart health diagnosis (e.g., clinical heart health diagnosis 306) to generate a dataset (e.g., machine-readable dataset 308) that defines such associations between discrete waveform portions (e.g., the PR Interval portion, the QRS complex portion, the QT interval portion, the ST segment portion, and the PR segment portion) and clinical heart health diagnosis (e.g., clinical heart health diagnosis 306). As discussed above, examples of such associations may include but are not limited to: Portion A of a first patient's specimen heartbeat waveform was elevated by over 50% and they had a heart attack; Portion A of a second patient's specimen heartbeat waveform was elevated by less than 20% and they did not have a heart attack; Portion B of a third patient's specimen heartbeat waveform was elevated by over 80% and they had a heart attack; and Portion B of a fourth patient's specimen heartbeat waveform was elevated by less than 40% and they did not have a heart attack.

As discussed above, when associating 402 at least one of the plurality of discrete waveform portions (e.g., the PR Interval portion, the QRS complex portion, the QT interval portion, the ST segment portion, and the PR segment portion) of each specimen heartbeat waveform (e.g., specimen heartbeat waveform 304) with the related clinical heart health diagnosis (e.g., clinical heart health diagnosis 306), waveform analysis process 10 may utilize 404 machine learning (e.g., machine learning/artificial intelligence/probabilistic modelling) to associate at least one of the plurality of discrete waveform portions (e.g., the PR Interval portion, the QRS complex portion, the QT interval portion, the ST segment portion, and the PR segment portion) of each specimen heartbeat waveform (e.g., specimen heartbeat waveform 304) with the related clinical heart health diagnosis (e.g., clinical heart health diagnosis 306).

For example and when associating 402 at least one of the plurality of discrete waveform portions (e.g., the PR Interval portion, the QRS complex portion, the QT interval portion, the ST segment portion, and the PR segment portion) of each specimen heartbeat waveform (e.g., specimen heartbeat waveform 304) with the related clinical heart health diagnosis (e.g., clinical heart health diagnosis 306), waveform analysis process 10 may identify 406 at least one of the plurality of discrete waveform portions (e.g., the PR Interval portion, the QRS complex portion, the QT interval portion, the ST segment portion, and the PR segment portion) of each specimen heartbeat waveform (e.g., specimen heartbeat waveform 304) that is at least partially responsible for the related clinical heart health diagnosis (e.g., clinical heart health diagnosis 306). Again, examples of such associations may include but are not limited to: Portion A of a first patient's specimen heartbeat waveform was elevated by over 50% and they had a heart attack; Portion A of a second patient's specimen heartbeat waveform was elevated by less than 20% and they did not have a heart attack; Portion B of a third patient's specimen heartbeat waveform was elevated by over 80% and they had a heart attack; and Portion B of a fourth patient's specimen heartbeat waveform was elevated by less than 40% and they did not have a heart attack General As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method, executed on a computing system, comprising:
receiving a single-lead heartbeat waveform for a user;
generating, via machine learning, one or more waveform features from a data set of specimen waveform records, wherein each of the specimen waveform records includes a specimen heartbeat waveform and a related clinical heart health diagnosis, generating the one or more waveform features including:
associating one or more discrete portions of each specimen heartbeat waveform with the related clinical heart health diagnosis; and
deriving a probabilistic outcome correlation between the one or more discrete portions of each specimen heartbeat waveform and the related clinical heart health diagnosis,
associating a heart health indicator with the single-lead heartbeat waveform including comparing one or more portions of the single-lead heartbeat waveform to the one or more waveform features, wherein the heart health indicator indicates whether the user is likely having a heart attack;
providing the heart health indicator to a recipient; and
notifying the user if they are likely having a heart attack.

2. The computer-implemented method of claim 1 wherein comparing one or more portions of the single-lead heartbeat waveform to one or more waveform features includes:
 comparing an ST segment portion of the single-lead heartbeat waveform to one or more ST segment waveform features.

3. The computer-implemented method of claim 1 wherein receiving a single-lead heartbeat waveform includes:
 receiving the single-lead heartbeat waveform from an external device.

4. The computer-implemented method of claim 1 wherein the single-lead heartbeat waveform is obtained via a differential voltage potential measurement concerning the heart of the user.

5. The computer-implemented method of claim 4 wherein the differential voltage potential measurement concerning the heart of the user is obtained via a first electrode configured to be touched by a first appendage of the user and a second electrode configured to be touched by a second appendage of the user.

6. The computer-implemented method of claim 1 wherein the heart health indicator is configured to indicate whether the user is having a heart attack.

7. The computer-implemented method of claim 1 wherein the recipient of the heart health indicator is the user.

8. The computer-implemented method of claim 1 wherein the recipient of the heart health indicator is a third party.

9. The computer-implemented method of claim 1 wherein associating a heart health indicator with the single-lead heartbeat waveform includes:
 providing the single-lead heartbeat waveform to an external computing environment;
 utilizing the external computing environment to associate the heart health indicator with the single-lead heartbeat waveform; and
 receiving the heart health indicator from the external computing environment.

10. A computer program product residing on a non-transitory computer readable medium having a plurality of instructions stored thereon which, when executed by a processor, cause the processor to perform operations comprising:
 receiving a single-lead heartbeat waveform for a user;
 generating, via machine learning, one or more waveform features from a data set of specimen waveform records, wherein each of the specimen waveform records includes a specimen heartbeat waveform and a related clinical heart health diagnosis, generating the one or more waveform features including:
  associating one or more discrete portions of each specimen heartbeat waveform with the related clinical heart health diagnosis; and
  deriving a probabilistic outcome correlation between the one or more discrete portions of each specimen heartbeat waveform and the related clinical heart health diagnosis,
 associating a heart health indicator with the single-lead heartbeat waveform including comparing one or more portions of the single-lead heartbeat waveform to the one or more waveform features, wherein the heart health indicator indicates whether the user is likely having a heart attack;
 providing the heart health indicator to a recipient; and
 notifying the user if they are having a heart attack.

11. The computer program product of claim 10 wherein comparing one or more portions of the single-lead heartbeat waveform to one or more waveform features includes:
 comparing an ST segment portion of the single-lead heartbeat waveform to one or more ST segment waveform features.

12. The computer program product of claim 10 wherein receiving a single-lead heartbeat waveform includes:
 receiving the single-lead heartbeat waveform from an external device.

13. The computer program product of claim 10 wherein the single-lead heartbeat waveform is obtained via a differential voltage potential measurement concerning the heart of the user.

14. The computer program product of claim 13 wherein the differential voltage potential measurement concerning the heart of the user is obtained via a first electrode configured to be touched by a first appendage of the user and a second electrode configured to be touched by a second appendage of the user.

15. The computer program product of claim 10 wherein the heart health indicator is configured to indicate whether the user is having a heart attack.

16. The computer program product of claim 10 wherein the recipient of the heart health indicator is the user.

17. The computer program product of claim 10 wherein the recipient of the heart health indicator is a third party.

18. The computer program product of claim 10 wherein associating a heart health indicator with the single-lead heartbeat waveform includes:
 providing the single-lead heartbeat waveform to an external computing environment;
 utilizing the external computing environment to associate the heart health indicator with the single-lead heartbeat waveform; and
 receiving the heart health indicator from the external computing environment.

19. A computing system including a processor and memory configured to perform operations comprising:
 receiving a single-lead heartbeat waveform for a user;
 generating, via machine learning, one or more waveform features from a data set of specimen waveform records, wherein each of the specimen waveform records includes a specimen heartbeat waveform and a related clinical heart health diagnosis, generating the one or more waveform features including:
  associating one or more discrete portions of each specimen heartbeat waveform with the related clinical heart health diagnosis; and
  deriving a probabilistic outcome correlation between the one or more discrete portions of each specimen heartbeat waveform and the related clinical heart health diagnosis,
 associating a heart health indicator with the single-lead heartbeat waveform including comparing one or more portions of the single-lead heartbeat waveform to the one or more waveform features, wherein the heart health indicator indicates whether the user is likely having a heart attack;
 providing the heart health indicator to a recipient; and
 notifying the user if they are having a heart attack.

20. The computing system of claim 19 wherein comparing one or more portions of the single-lead heartbeat waveform to one or more waveform features includes:
 comparing an ST segment portion of the single-lead heartbeat waveform to one or more ST segment waveform features.

21. The computing system of claim 19 wherein receiving a single-lead heartbeat waveform includes:

receiving the single-lead heartbeat waveform from an external device.

22. The computing system of claim 19 wherein the single-lead heartbeat waveform is obtained via a differential voltage potential measurement concerning the heart of the user.

23. The computing system of claim 22 wherein the differential voltage potential measurement concerning the heart of the user is obtained via a first electrode configured to be touched by a first appendage of the user and a second electrode configured to be touched by a second appendage of the user.

24. The computing system of claim 19 wherein the heart health indicator is configured to indicate whether the user is having a heart attack.

25. The computing system of claim 19 wherein the recipient of the heart health indicator is the user.

26. The computing system of claim 19 wherein the recipient of the heart health indicator is a third party.

27. The computing system of claim 19 wherein associating a heart health indicator with the single-lead heartbeat waveform includes:
   providing the single-lead heartbeat waveform to an external computing environment;
   utilizing the external computing environment to associate the heart health indicator with the single-lead heartbeat waveform; and
   receiving the heart health indicator from the external computing environment.

* * * * *